United States Patent [19]

Tolentino

[11] 4,448,981
[45] May 15, 1984

[54] METHOD OF MAKING ORGANOSILOXANES AND ALKYL HALIDES FROM DIALKYLDIALKOXYSILANES

[75] Inventor: Luisito A. Tolentino, Ballston Lake, N.Y.

[73] Assignee: General Electric Company, Waterford, N.Y.

[21] Appl. No.: 494,191

[22] Filed: May 13, 1983

[51] Int. Cl.³ .............................................. C07F 7/08
[52] U.S. Cl. ..................................... 556/459; 556/460
[58] Field of Search .............................. 556/460, 459

[56] References Cited

U.S. PATENT DOCUMENTS

| | | | |
|---|---|---|---|
| 2,384,384 | 9/1945 | McGregor et al. | 556/460 |
| 2,439,856 | 4/1948 | McGregor et al. | 556/460 |
| 2,465,547 | 3/1949 | McGregor et al. | 556/460 |
| 2,719,859 | 10/1955 | Nitzche et al. | 556/460 |
| 2,731,485 | 1/1956 | Wagner et al. | 556/452 |
| 2,902,507 | 9/1959 | Hyde et al. | 556/452 |
| 3,008,975 | 11/1961 | Schubert | 556/471 |
| 3,465,016 | 9/1969 | Hampton | 556/460 |
| 3,567,756 | 3/1971 | Rothe | 556/477 |
| 3,607,898 | 9/1971 | Macher | 556/460 |
| 3,642,852 | 2/1972 | Rossmy et al. | 556/452 |
| 3,801,618 | 4/1974 | Walker | 556/471 |
| 3,846,464 | 11/1974 | Razzano | 556/460 |
| 3,983,148 | 9/1976 | Reedy et al. | 556/460 |
| 4,073,801 | 2/1978 | Moretto et al. | 556/452 |
| 4,108,882 | 8/1978 | Mahone | 556/460 |
| 4,113,760 | 9/1978 | Frey et al. | 556/460 X |
| 4,161,487 | 7/1979 | Borner et al. | 556/452 |
| 4,366,324 | 12/1982 | Habata et al. | 556/460 |

*Primary Examiner*—Paul F. Shaver
*Attorney, Agent, or Firm*—E. F. Chapman; G. L. Loser; J. L. Young

[57] ABSTRACT

An improved process for making an alkyl halide and organosiloxanes from a dialkyldialkoxysilane and a hydrogen halide is disclosed. Dialkyldialkoxysilane and hydrogen halide are simultaneously introduced at respective feed points into a column containing hydrogen halide under reflux in such proportions that the amount of hydrogen halide introduced into the column is at a stoichiometric excess over the dialkyldialkoxysilane. In preferred embodiments, the hydrogen halide is hydrogen chloride; the dialkyldialkoxysilane is dimethyldimethoxysilane; the alkyl halide is methyl chloride; and the organosiloxanes are predominantly of the cyclic type.

25 Claims, No Drawings

METHOD OF MAKING ORGANOSILOXANES AND ALKYL HALIDES FROM DIALKYLDIALKOXYSILANES

BACKGROUND OF THE INVENTION

The present invention relates to a process for simultaneously preparing organosiloxanes and alkyl halides from the corresponding dialkyldialkoxysilane, and more particularly, to a process for controlling the organosiloxane and alkyl halide products from the reaction of dialkyldialkoxysilanes and hydrogen halides.

Generally, organopolysiloxanes are made by the hydrolysis of one or a mixture of organochlorosilanes to form silanes having silanol groups, which, in turn, form silanol condensation products to produce the organopolysiloxanes. The organopolysiloxanes are useful as lubricants and for the preparation of high molecular weight silicone products by conventional and well-known methods.

One of the by-products formed by the hydrolysis of the organochlorosilane is hydrogen chloride. In commercial practice, aqueous hydrogen chloride is distilled to recover the anhydrous form which is reacted with methyl alcohol to produce water and methyl chloride. The methyl chloride is further used to produce alkylchlorosilanes by reacting the methyl chloride with metallic silicon. In the foregoing method, the organopolysiloxanes and the methyl chloride are generally produced in two separate processes.

The concurrent preparation of methyl chloride and organosiloxanes has been proposed and is disclosed in U.S. Pat. No. 4,366,324. In U.S. Pat. No. 4,366,324, there is a direct reaction between an organohalogenosiloxane and an alkanol to produce an alkyl halide and organopolysiloxanes, or, more particularly, there is a direct reaction between an organochlorosilane and methyl alcohol to produce organopolysiloxanes and methyl chloride. By this process, large volumes of hydrochloric acid are avoided, however, generally, the organochlorosilanes used for hydrolysis contain methyltricholosilane which is responsible for the formation of gels. Thus, it is desirable to provide a process wherein the starting materials are free of tri-functional impurities, such as methyltrichlorosilane, to avoid the formation of tri-functional sites upon monomers which are responsible for the formation of the gels.

Various processes have been proposed for making organopolysiloxanes from dialkyldialkoxysilanes. In U.S. Pat. No. 2,465,547, the cyclic octomer, hexadecamethylcyclooctasiloxane, is produced in the acid catalyzed hydrolysis of dimethyldiethoxysilane or dimethyldichlorosilane. The dimethyldiethoxysilane is mixed with one volume of a mixture of 95% ethyl alcohol and concentrated aqueous hydrochloric acid in equal parts to prepare the cyclic polymer after the reaction mixture is refluxed for about 4 to 8 hours. The polymer product is a mixture of cyclic polymers of dimethylsiloxane having up to 13 silicon atoms per molecule. The cyclic octamer is obtained at certain temperatures and pressures by distillation.

In a similar process, as described in U.S. Pat. No. 2,384,384, dimethyl diethoxy silicane dissolved in ethyl alcohol, is hydrolyzed with water, and preferably, the hydrolysis is carried out in the presence of an acid catalyst by mixing one volume of the dimethyldiethoxysilicane with one volume of a mixture of 95% ethyl alcohol and concentrated aqueous hydrochloric acid in equal parts to prepare mixtures of dimethylsilicone polymers, the lower polymers containing up to about 8 of the siloxane structural units wherein the siloxane units are joined in a ring of siloxane linkages. The hydrolysis by this method is disadvantageous for the continuous production of silicones because the reaction mixture must be refluxed for at least 1 hour and, more preferably, about 4 to 8 hours, to obtain the products. Furthermore, the process of U.S. Pat. No. 2,384,384 is disadvantageous because ethyl alcohol must be added to the reaction mixture, and little or no alkyl halide is formed as a result of the reaction because only catalytic amounts of the aqueous hydrochloric acid are used.

Reactions between tri-functional silanes, such as trimethoxysilane, and hydrogen chloride are disclosed in U.S. Pat. No. 3,567,756. However, the products of the reaction are monochlorotrimethoxysilane and hydrogen. Furthermore, as discussed above, dialkyldialkoxysilanes having trifunctional impurities promote the formation of gels upon hydrolysis. Accordingly, any trifunctional alkoxysilane impurity in the dialkyldialkoxysilane monomer is disadvantageous in the production of organopolysiloxanes.

Alternative hydrolysis methods and methods of making polysiloxanes from dialkyldialkoxysilanes are disclosed in U.S. Pat. No. 2,439,856, U.S. Pat. No. 2,719,859 and U.S. Pat. No. 2,731,485. The processes disclosed in these patents generally have most of the same disadvantages discussed above. Other processes and the disadvantages thereof, are disclosed and discussed in U.S. Pat. No. 4,366,324 briefly discussed above.

SUMMARY OF THE INVENTION

It is the primary object of the present invention to provide an improved process for making an alkyl halide and organosiloxanes.

It is another object of the present invention to provide an improved process for making an alkyl halide and organosiloxanes from a dialkyldialkoxysilane and a hydrogen halide.

It is another object of the present invention to provide a process for improving the amount of alkyl halide produced from the reaction of dialkyldialkoxysilanes and hydrogen halides.

Still another object of the present invention is to provide a process for improving the amount of cyclic organosiloxanes obtained from the reaction of dialkyldialkoxysilanes and hydrogen halides.

A further object of the present invention is to provide a process for improving the amount of linear organosiloxanes produced from the reaction of dialkyldialkoxysilanes and hydrogen halides.

Another object of the present invention is to provide a process for controlling the amount of alkyl halide product and the amount and type of organosiloxane product in the reaction of a dialkyldialkoxysilane and a hydrogen halide.

Still another object of the present invention is to provide a process for reacting a dialkyldialkoxysilane and a hydrogen halide wherein the halide content is substantially converted to alkyl halide, and there is only minimal hydrolyzable halide in the product.

Other objects and advantages of the invention will become apparent as the description thereof proceeds.

These and other objects of the invention are achieved by providing a process for making an alkyl halide and organosiloxanes from a dialkyldialkoxysilane and a hydrogen halide, comprising, simultaneously introducing the dialkyldialkoxysilane and hydrogen halide into a column containing hydrogen halide under reflux in such proportions that the amount of hydrogen halide introduced into the column is at a stoichiometric excess relative to the dialkyldialkoxysilane introduced into the column. The dialkyldialkoxysilane is introduced into the column at one or a plurality of feed points located between the top of the column and the bottom of the column, and the hydrogen halide is introduced into the column at one or a pluralitiy of feed points located between the top of the column and the bottom of the column.

In another embodiment of the present invention, there is provided a process for controlling the amount of alkyl halide product and the amount and type of organosiloxane product in the reaction of a dialkyldialkoxysilane and a hydrogen halide, comprising:

(a) providing hydrogen halide under reflux in a column having at least one dialkyldialkoxysilane feed point and at least one hydrogen halide feed point between the top of the column and the bottom of the column;

(b) varying the location of the respective hydrogen halide and dialkyldialkoxysilane feed points in the column;

(c) introducing hydrogen halide and dialkyldialkoxysilane into the column in such proportions that the amount of hydrogen halide introduced into the column is at a stoichiometric excess relative to the dialkyldialkoxysilane introduced into the column; and (d) varying the stoichiometric excess of the hydrogen halide.

In accordance with the present invention, it has been found that up to 99.9% yields of alkyl halide, for example, methyl chloride can be obtained in accordance with the present invention when a dialkyldialkoxysilane is reacted with a stoichiometric excess of hydrogen halide in a reflux column containing hydrogen halide under reflux. Furthermore, it has been found in accordance with the process of the present invention that the composition of the organosiloxane products can be controlled by varying the reaction conditions, and that reaction conditions can be varied so that the organosiloxane product resulting from the reaction, contains a high percentage of cyclic organosiloxanes or a high percentage of linear organopolysiloxanes.

Although I do not wish to be bound by any theory, the chemical reaction of the present process appears to occur as set forth in the following three equations:

$$(CH_3)_2Si(OCH_3)_2 + HCl \rightleftharpoons (CH_3)_2Si(OCH_3)Cl + CH_3OH \quad (1)$$

$$CH_3OH + HCl \rightarrow H_2O + CH_3Cl \quad (2)$$

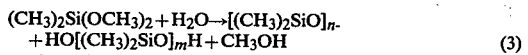
$$(CH_3)_2Si(OCH_3)_2 + H_2O \rightarrow [(CH_3)_2SiO]_n + HO[(CH_3)_2SiO]_mH + CH_3OH \quad (3)$$

Equation (1) shows the reaction between a typical dialkyldialkoxysilane, such as, dimethyldimethoxysilane and a typical hydrogen halide, such as, hydrogen chloride, in a reflux column containing hydrogen halide under reflux to produce the corresponding alkanol, such as, methanol, and the corresponding monohalomonomethoxydimethylsilane, such as, mono- chloromonomethoxydimethylsilane. In accordance with the present invention, only trace quantities of the monohalomonoalkoxydialylsilane are found in the final product. Equation (2) shows the reaction of the alkanol produced in equation (1) with the hydrogen halide to produce water and alkyl halide, for example, methyl chloride, product. Equation (3) shows the hydrolysis of the dialkyldialkoxysilane with water produced in equation (2) to form cyclic organopolysiloxanes having the general formula $[(CH_3)_2SiO]_n$ and linear organopolysiloxanes designated as $HO[(CH_3)_2SiO]_mH$.

Generally, the cyclic polymers, formed from dialkyldialkoxysilane may have up to 13 silicon atoms per molecule, and accordingly, n in the formula of equation (3) above representing cyclic organosiloxane product would be from about 3 to about 13. However, in accordance with the present invention, it has been found that n is generally about 3 to about 7, and that in most cases n is 4 and 5. In preferred embodiments in the process of the present invention, the cyclic product is the tetramer and the pentamer, and minor amounts of cyclic trimer, cyclic hexamer and cyclic heptamer are formed. Less than about 1% of the product comprises cyclic polymers having from about 8 to about 13 silicon atoms per molecule. Generally, in accordance with the process of the present invention, the octamethylcyclotetrasiloxane is the predominant cyclic polymer formed in the process.

In the linear organosiloxane products prepared in accordance with the process of the present invention and shown in equation (3) above, m is about 2 to about 20 siloxane units per molecule, that is, about 2 to about 20 silicon atoms per molecule. Generally, the linear products made by the process of the present invention are silanol-stopped polymers.

As used herein, the terms "organopolysiloxanes", "polysiloxanes" and "organosiloxanes", whether cyclic or linear, are used interchangeably.

DETAILED DESCRIPTION OF THE INVENTION

The hydrolyzable silanes which may be used as the starting materials in the process of the present invention, are substantially pure dialkyldialkoxysilanes free of tri-functional impurities and generally free of chlorine. Although any dialkyldialkoxysilane may be used in the process of the present invention, the preferred hydrolyzable silane material which is reacted with hydrogen chloride in a column containing hydrogen chloride under reflux, is dimethyldimethoxysilane. Other preferred dialkyldialkoxysilanes include those having alkyl groups with about 1 to about 12 carbon atoms and those having alkoxy groups with about 1 to about 12 carbon atoms, for example, dimethyldiethoxysilane, diethyldimethoxysilane, and the like. Furthermore, mixtures of the dialkyldialkoxysilanes may also be used in the present processes. Naturally, the alkyl group of the corresponding alkyl halide and the alkyl group of the corresponding organosilane product depends upon the alkyl group or groups present in the dialkyldialkoxysiloxane product. Furthermore, the alkyl group of the corresponding alkanol and the alkyl group of the corresponding alkyl halide depends upon the alkoxy group or alkoxy groups of the dialkyldialkoxysilane starting material.

Any of the hydrogen halides may be used as the starting material in the process of the present invention. Although hydrogen chloride is the preferred starting hydrogen halide material, the process of the present invention may also be carried out with the other hydrogen halides including hydrogen bromide, hydrogen iodide and hydrogen fluoride. The hydrogen halide may be anhydrous and in the form of a gas, or it may be aqueous in the form of a solution. When aqueous hydrogen chloride is used in the process of the present invention, any suitable concentration of aqueous hydrogen halide may be used as a starting material. For example, in certain preferred embodiments, the aqueous hydrogen halide may range from as low as 1% up to about 37% by weight hydrogen halide or hydrogen chloride in water. Since either anhydrous hydrogen chloride or aqueous hydrogen chloride may be used in the process of the present invention, there is no limitation upon the lower limit of the concentration of aqueous hydrogen chloride, and the upper limit of the concentration of aqueous hydrogen chloride is limited only by the type of equipment used in carrying out the reaction and the handling difficulties when high concentrations are utilized.

In all cases, in the process of the present invention, it is important that an excess of anhydrous hydrogen chloride or aqueous hydrogen chloride be utilized in the reaction to achieve the objects of the present invention. In the broadest aspects of the present invention, any excess of hydrogen chloride greater than about 5% may be utilized, however, in more preferred embodiments, an excess of about 15% to about 75% hydrogen chloride may be utilized. Since the process for controlling the amount of alkyl halide product and the amount and type of organosiloxane product in the reaction of the dialkyldialkoxysilane and hydrogen halide depends upon varying the stoichiometric excess of the hydrogen halide, it is critical to provide for the appropriate excess of hydrogen chloride to obtain a desired type of product or a desired yield of product. For example, a 99.9% yield of methyl chloride is obtained when a 50% excess of aqueous hydrogen chloride is fed into the reflux column to react with the dimethyldimethoxysilane being fed into the reflux column.

The stoichiometric excess of the hydrogen halide may be provided by any appropriate means, and generally, in accordance with the preferred embodiments of the present invention, the hydrogen chloride is metered into the reflux or reactor column at the desired feed rate generally measured in grams per minute. The dialkyldialkoxysilane may also be provided in the reflux or reactor column by any appropriate method, and generally, in the preferred embodiments of the present invention, the dialkyldialkoxysilane is metered into the reflux or reactor column at a given feed rate generally designated in grams per minute.

Since the dialkyldialkoxysilane and hydrogen halide are simultaneously introduced into a column containing hydrogen halide under reflux, hydrogen halide may be provided under reflux in the column by heating aqueous hydrogen chloride in a reboiler connected to the reflux column. The heating of the aqueous hydrogen halide in the reboiler may be initiated prior to the introduction of the dialkyldialkoxysilane and hydrogen halide into the column. When aqueous hydrogen halide is not provided under reflux from a reboiler, it is possible to provide the hydrogen halide under reflux in the column by introducing the hydrogen halide from a suitable feed point located in the column, and suitable heat to maintain the hydrogen halide under reflux may be provided by heating elements used in conjunction with the column to provide a heated column. Naturally, it is also possible in accordance with the process of the present invention to provide hydrogen halide under reflux in the column by a combination of the foregoing methods.

Generally, the temperature of the reaction of the dialkyldialkoxysilane and hydrogen halide is that temperature which is sufficient to reflux the hydrogen halide in the reflux column. In order to achieve a temperature sufficient to reflux the hydrogen halide introduced into the column, the hydrogen halide is preferably heated at about 120° C. to about 175° C., and more preferably at about 150° C. to about 175° C., especially when the hydrogen halide is hydrogen chloride. Optimal temperature profiles to maintain the hydrogen halide under reflux for the desired reaction may be easily determined for each of the hydrogen halides by examining the boiling points of the respective hydrogen halide.

One of the methods of heating the hydrogen halide at the appropriate temperature is by providing a reboiler containing hydrogen halide and heating the reboiler containing the hydrogen halide at a temperature suffient to cause the hydrogen halide in the reboiler to reflux in the column. Once the hydrogen halide is under reflux in the column, the dialkyldialkoxysilane and hydrogen halide reactants are introduced into the column while the temperature sufficient to cause the hydrogen halide in the reboiler to reflux and thereby provide sufficient heat for the reaction, is maintained. As indicated above, the temperature at which the hydrogen halide is heated in the reboiler is between about 120° C. to about 175° C., and more preferably at about 150° C. to about 175° C., when the hydrogen halide is aqueous hydrogen chloride.

In certain embodiments, the reflux column itself can be heated to achieve a temperature sufficient to provide the heat for the reaction of the dialkyldialkoxysilane and hydrogen halide in accordance with the process of the present invention. The column can be heated by any suitable heating means well-known in the art, and the appropriate amount of heat can be applied to the column to provide a temperature sufficient to reflux the hydrogen halide introduced into the column, which in the case of hydrogen chloride is about 120° C. to about 175° C., and more preferably, about 150° C. to about 175° C. In the case where the column is heated, and there is no reboiler attached thereto, it is preferred to feed aqueous instead of anhydrous hydrogen halide into the reflux column to provide appropriate conditions for maintaining the hydrogen halide under reflux. Alternatively, when a reboiler is utilized, it is preferred that aqueous hydrogen halide be used in the reboiler to provide the hydrogen halide under reflux in the reflux or reactor column, and the hydrogen halide reactant introduced into the reflux or reactor column at a feed point located between the top of the column and the bottom of the column, can be aqueous hydrogen halide or anhydrous hydrogen halide, the hydrogen halide reactant being introduced into the column at a stoichiometric excess of about 15% to about 75% over the dialkyldialkoxysilane introduced into the column.

In one preferred embodiment of the present invention, when a reflux column or reactor column and a reboiler are utilized and the temperature profile is controlled in each one-third section of the column, when dimethyldimethoxysilane is the dialkyldikoxysilane, and when hydrogen chloride is the aqueous hydrogen halide, and aqueous hydrogen chloride is utilized in the reboiler and maintained under reflux at a temperature of about 150° C. to about 175° C. in the reboiler, the temperature profile of the reactor column or reflux column is about 120° C. in the bottom one-third section of the column, that is, the section of the column nearest the reboiler; about 100° C. in the middle section of the column; and about 80° C. in the top one-third section of the column. Naturally, any of these temperatures can be controlled or varied in accordance with the process of the present invention by varying the heat in the reboiler or by varying the heat applied to the reflux column or reactor column, or both, as desired.

In one embodiment of the present invention, when the dialkyldialkoxysilane is introduced into the column at a feed point located between the top of the column and the bottom of the column, and the hydrogen halide is introduced into the column at a feed point located between the top of the column and the bottom of the column while the hydrogen halide is maintained at reflux at a temperature of about 150° C. to about 175° C., the yield of alkyl halide improves as the amount of hydrogen halide is increased from about a 15% to about a 60% stoichiometric excess over the amount of dialkyldialkoxysilane. When dimethyldimethoxysilane and hydrogen chloride are both introduced into the reflux column at feed points located in the upper region of the column, that is, in the upper one-third or upper one-half of the column, while the hydrogen halide is maintained at reflux at a temperature of about 150° C. to about 175° C., the yield of methyl chloride improves as the amount of hydrogen chloride is increased from about a 15% to about a 60% stoichiometric excess over the amount of dimethyldimethoxysilane, and maximum yields of methyl chloride are obtained under the foregoing conditions when the hydrogen chloride reaches a stoichiometric excess of about 50% over the amount of dimethyldimethoxysilane introduced into the reflux column.

In one preferred embodiment of the present invention, when dimethyldimethoxysilane is introduced into the column at a feed point located in the upper region of the column; the hydrogen chloride is introduced into the column at a feed point located in the lower region of the column; and the hydrogen chloride is maintained at reflux at a temperature of about 150° C. to about 175° C., the yield of cyclic organosiloxanes is greater than about 70% by weight of the organosiloxane composition when the hydrogen chloride is fed into the column at a stoichiometric excess of about 15% to about 50% over the amount of dimethyldimethoxysilane fed into the column.

As used herein, "upper region" of the reflux column or reactor column is generally about the upper one-half of the column, and more preferably, about the upper one-third of the column, while "lower region" of the reflux or reactor column is generally about the lower one-half of the column, and more preferably, about the lower one-third of the column. The lower region of the reflux or reactor column is the region proximal the reboiler in those cases where a reboiler is utilized, or in those cases where there is no reboiler and a collector is utilized to collect the organosiloxane products, the lower region of the column is the region proximal the product collector.

In accordance with the above discussion, it can be seen that the location of the feed points for the hydrogen halide and the dialkyldialkoxysilane is not critical to the formation of the products in general, however, by varying the location of the respective hydrogen halide and dialkyldialkoxysilane feed points in the column, it is possible to vary the amount of alkyl halide product and the composition of the organopolysiloxane product. When the respective feed points are in the upper region of the reflux column or reactor column, for example, in the upper one-third section of the reactor column, the yield of alkyl halide is generally high and/or the amount of cyclic product of the organopolysiloxane composition is high. However, when the respective hydrogen halide and dialkyldialkoxysilane feed points are both located in the lower regions of the reflux column or reactor column, for example, in the lower one-third section of the reactor column, the yield of the linear organopolysiloxanes is substantially higher than the yield of cyclic organopolysiloxanes. In one specific embodiment of the present invention, when hydrogen chloride and dimethyldimethoxysilane are introduced into the column at respective feed points located in the lower region of the column, and the hydrogen chloride is introduced in an amount at from about a 15% to about a 75% stoichiometric excess over the amount of dimethyldimethoxysilane, the amount of organosiloxane products of the linear type is substantially greater than the amount of the cyclic type. It has also been found that when the hydrogen halide feed point is in the upper region of the reactor column, for example, in the upper one-third section of the reactor column, and the dialkyldialkoxysilane feed point is in the lower region of the column, for example, in the lower one-third section of the reactor column, there is a high yield of alkyl halide, and the organopolysiloxanes of the cyclic type are the predominant organopolysiloxane in the composition.

The rate at which the hydrogen halide and the dialkyldialkoxysilane are fed into the reactor column or reflux column is not critical as long as there is a stoichiometric excess (as discussed above) of hydrogen halide introduced into the column. Although it is not meant to be a limitation, generally, to maintain the desired excess of hydrogen halide in the reactor column, the hydrogen halide is fed into the reactor column at a feed rate of one to about four times greater than the feed rate of the dialkyldialkoxysilane. For example, when the feed rate of dimethyldimethoxysilane is 0.9 g/min, a desirable feed rate for introducing aqueous hydrogen chloride into the reactor column to maintain a 50% stoichiometric excess of hydrogen chloride over dimethyldimethoxysilane is 2.2 g/min when the hydrogen chloride is a 37% aqueous hydrogen chloride.

The number of feed points for introducing the hydrogen halide and the dialkyldialkoxysilane into the reactor column or reflux column is not critical as long as the appropriate excess of hydrogen halide is maintained in the reactor column and as long as the desired amount of alkyl halide product and the desired amount and type of organopolysiloxane product are obtained. For example, in a preferred embodiment of the present invention, one aqueous hydrogen chloride feed point is used to introduce aqueous hydrogen chloride into the reactor column, and one dialkyldialkoxysilane feed point is utilized to introduce dimethyldimethoxysilane into the reactor column. However, any plurality of either hydrogen halide feed points or dialkyldialkoxysilane feed points may be used in accordance with the process of the present invention, and there can be a greater number of one type of feed than the other type. For example, there can be two hydrogen halide feed points and only one dialkyldialkoxysilane feed point. Furthermore, any combination of locations of feed points may be used for introducing the respective reactants into the reactor column, for example, one feed stream of hydrogen halide may be introduced into the upper one-third of the column, and another feed stream of the hydrogen halide may be located in the lower one-third of the reactor column while the feed point for the dialkyldialkoxysilane is located in the upper one-third of the reactor column. In another embodiment, hydrogen halide may be introduced into the middle one-third of the reactor column, while dialkyldialkoxysilane is introduced into the upper one-third of the column and into the lower one-third of the column. From the foregoing, it can be seen that many variations of feed point locations may be utilized in accordance with the process of the present invention to introduce hydrogen halide and dialkyldialkoxysilane into the reactor column.

In preferred embodiments of the present invention, there is provided a process for controlling the amount of alkyl halide product and the amount and type of organosiloxane product in the reaction of a dialkyldialkoxysilane and a hydrogen halide, by providing the hydrogen halide, preferably an aqueous hydrogen halide, under reflux in a column having at least one dialkyldialkoxysilane feed point and at least one hydrogen halide feed point; varying the location of the respective hydrogen halide and dialkyldialkoxysilane feed points in the column; introducing the hydrogen halide and dialkyldialkoxysilane into the column in such proportions that the amount of hydrogen halide introduced into the column is at a stoichiometric excess relative to the dialkyldialkoxysilane; and varying the stoichiometric excess of the hydrogen halide. In a preferred embodiment of the present invention, the hydrogen halide is hydrogen chloride, and the dialkyldialkoxysilane is dimethyldimethoxysilane. Along with the foregoing variables for controlling the amount of alkyl halide product and the amount and type of organosiloxane product, the heat of the reaction can also be varied, that is, the temperature of the hydrogen halide under reflux in the column can be varied. This has been discussed in detail above, and when the hydrogen halide is hydrogen chloride, the column temperature can vary between about 80° C. and about 175° C., and preferably, between about 80° C. in the top one-third section of the column to about 120° C. in the bottom one-third section of the column with a temperature of about 100° C. in the middle one-third section of the column while the reboiler temperature is maintained at about 150° C. to about 175° C.

When the hydrogen halide and the dialkyldialkoxysilane are introduced into the column at respective feed points located in the upper region of the column, and the amount of hydrogen halide is introduced at from about a 15% to about a 60% stoichiometric excess over the amount of dialkyldialkoxysilane, the amount of alkyl halide product is increased, and amount of organosiloxane products of the cyclic type is substantially greater than the linear type, that is, the amount of cyclic type organopolysiloxane is about 1.5 to about 3.0 times greater than that of the linear type. When the hydrogen halide and the dialkyldialkoxysilane are introduced into the column at respective feed points in the column, one of which respective feed points is located in the upper region of the column, for example, in the upper one-third section of the column, and the other of which respective feed points is located in the lower region of the column, that is, in the lower one-third region of the column, and the amount of hydrogen halide introduced into the column is from about a 15% to about a 60% stoichiometric excess over the amount of dialkyldialkoxysilane, the amount of organopolysiloxane product of the cyclic type is substantially greater than the amount of the linear type, that is, about 1.5 to about 3 times greater. When the hydrogen halide and the dialkyldialkoxysilane are introduced into the column at respective feed points located in the lower region of the column, and the hydrogen halide is introduced in an amount at from about a 15% to about a 75% stoichiometric excess over the amount of dialkyldialkoxysilane, the amount of organopolysiloxane product of the linear type is substantially greater than the amount of the cyclic type, for example, the amount of linear type is about 5.0 to about 10.0 times greater than the amount of the cyclic type.

In one preferred embodiment in accordance with at least some of the objects of present invention, there is provided a process for controlling the amount of methyl chloride product and the amount and type of cyclic and linear organosiloxane product in the reaction of a dimethyldimethoxysilane and hydrogen chloride, comprising:

(a) providing hydrogen chloride under reflux in a column having at least one dimethyldimethoxysilane feed point between the top of the column and the bottom of the column and at least one hydrogen chloride feed point between the top of the column and the bottom of the column; and (b) introducing hydrogen chloride and dimethyldimethoxysilane into the column at respective feed points located in the upper region of the column, the amount of hydrogen chloride being introduced at from about a 15% to about a 60% stoichiometric excess over the amount of dimethyldimethoxysilane, whereby the amount of methyl chloride product is increased, and the amount of organosiloxane product of the cyclic type is substantially greater than the linear type; or introducing hydrogen chloride and dimethyldimethoxysilane into the column at respective feed points in the column, one of which respective feed points is located in the upper region of the column and the other of which respective feed points is located in the lower region of the column, the amount of hydrogen chloride being introduced at from about a 15% to about a 60% stoichiometric excess over the amount of dimethyldimethoxysilane, whereby the amount of organosiloxane product of the cyclic type is substantially greater than the amount of the linear type; or introducing hydrogen chloride and dimethyldimethoxysilane into the column at respective feed points located in the lower region of the column, the amount of hydrogen chloride being introduced at from about a 15% to about a 75% stoichiometric excess over the amount of dimethyldimethoxysilane, whereby the amount of organosiloxane product of the linear type is substantially greater than the amount of the cyclic type.

The water to carry out the hydrolysis of the dialkyldialkoxysilane under acid conditions can be water derived from the aqueous hydrogen chloride in those cases where aqueous hydrogen chloride is utilized, or it can be water formed during the reaction, for example, from equation (2) shown above, or both. An alkanol, for example methanol, can also be added to initiate the reaction.

The solution emerging from the reactor column or reflux column after the reaction has been carried out is collected in a reboiler or a collector and may be transferred to a separator to recover the siloxanes. The acidic aqueous phase can be recycled to the reactor column or reflux column in a controlled manner. Naturally, the process of the present invention is one which is preferably carried out in a continuous manner, however, it can also be carried out under static conditions. By continuously introducing the reactants into the column containing hydrogen halide under reflux, product is continuously formed and can be continuously collected.

The cyclic organopolysiloxanes can be separated from the linear organopolysiloxanes produced by the process of the present invention by distillation, and the linear organopolysiloxanes can be returned to the reactor column or reflux column for further conversion to cyclic products.

The alkyl halide product, for example, methyl chloride, along with unreacted hydrogen halide, passes from the top of the column as an overhead product. The alkyl halide containing some unreacted hydrogen halide can be passed through a packed column reactor where the acid in the presence of alkanol, for example, methanol, is converted to alkyl halide, such as methyl chloride, and water. Hydrogen halide and water can be returned to the reactor column as desired.

The following examples are set forth to more fully and clearly illustrate the present invention and are intended to be, and should be construed as being, exemplary and not limitative of the invention. Unless otherwise stated, all parts and percentages are by weight.

EXAMPLES

The process was carried out in a reactor column 30.48 cm. (1 foot) by 1.27 cm. (0.5 inch). The column made from pyrex glass was electrically heated and equipped with four feed ports. The column was packed with 4 mm×4 mm ceramic saddles. Two water-cooled condensers were attached to the top of the reactor column and connected in series. The water passing through the water-cooled condensers was maintained at about 10° C. A 500-ml flask (reboiler) having a heating mantle was attached to the bottom of the reactor column, and provision was made for removal of product from the bottom of the flask.

The reactor column was heated by the electrical mantle, and the heat was maintained at the desired temperature by using a heat controller. The temperature of the reactor column is shown in degrees C. in the table below for each of the experiments conducted in accordance with the process of the present invention. The flask (reboiler) was charged with 50 ml. of aqueous hydrogen chloride and was heated to reflux. In the experiment shown in the table below, example number 1 utilized 20% aqueous hydrogen chloride and examples 2-6 utilized 37% aqueous hydrogen chloride. In the examples shown in the table below, a temperature of 96° C. to 102° C. was established in the reboiler, and this was sufficient to maintain the aqueous hydrogen chloride under reflux in the column. The experiments were run continuously for about 4 to about 5 hours.

A series of experiments were carried out under the conditions given in the table below. In each case, liquid dimethyldimethoxysilane and aqueous hydrogen chloride were fed separately into the reactor column using variable speed pumps. The organosiloxane products were collected in the flask (reboiler).

The products collected in the flask surprisingly displayed ease of separation of the aqueous phase from the siloxane phase. The separation of the aqueous phase from the siloxane phase in the reboiler flask are sufficient so that provision can be made to withdraw and separate the siloxane phase from the aqueous phase continuously from the flask. The aqueous phase contained about 19% to about 21% hydrogen chloride. Despite the fact that the siloxane phase was in contact with the acidic aqueous phase at an elevated temperature, the siloxane phase surprisingly showed low chloride content as shown in the table below under "Hydrolyzable Chloride in Siloxane".

The cyclic content of the organosiloxane composition was determined by gas chromatography using an internal standard. The linear content of the organosiloxane composition was obtained by subtracting the total cyclic content from the total organosiloxanes.

The gaseous overhead product which passed from the top of the reactor column, was passed through a water solution to trap the unreacted hydrogen chloride before venting the volatile methyl chloride. The total amount of unreacted hydrogen chloride was determined by acid titration of the aqueous phase, siloxane phase and overhead hydrogen chloride trap. By taking the difference between the charged and unreacted hydrogen chloride, it was possible to calculate the amount of hydrogen chloride which was converted to methyl chloride.

Gas chromatography analysis showed about 0.10% dimethyl ether in the methyl chloride vent gas.

The results of the experiments are shown in the table below where the feed location is measured from the top of the column reactor, and the respective feed locations were either 25.4 cm (10 inches) from the top of the column or 5.08 cm (2 inches) from the top of the column as shown in the table below.

TABLE

TABLE SHOWING REACTION CONDITIONS AND PRODUCTS BY REACTING DIMETHYLDIMETHOXYSILANE AND HYDROGEN CHLORIDE

| Example No | Reactor Temp. ° C. | (1) Feed Rate, g/min | | (2) Feed Location | | Organosiloxane Composition, Weight % | | (3) % Yield $CH_3Cl$ | Hydrolyzable Chloride in Siloxane ppm Cl |
|---|---|---|---|---|---|---|---|---|---|
| | | Aq. HCl | $(CH_3)_2Si(OCH_3)_2$ | Aq. HCl | $(CH_3)_2Si(OCH_3)_2$ | Cyclics | Linears | | |
| 1 | 150 | 2.5 (19% excess) | 0.7 | 25.4 cm. | 5.08 cm. | 70.4 | 29.6 | 32.6 | 730 |
| 2 | 150 | 1.3 (27% excess) | 0.6 | 5.08 cm. | 5.08 cm. | 60.0 | 40.0 | 73.9 | 270 |
| 3 | 150 | 1.3 (27% excess) | 0.6 | 25.4 cm. | 5.08 cm. | 71.7 | 28.3 | 78.6 | 700 |
| 4 | 150 | 2.2 (50% excess) | 0.9 | 5.08 cm. | 5.08 cm. | 67.6 | 32.4 | 99.9 | 500 |
| 5 | 120 | 2.8 (55% excess) | 1.1 | 5.08 cm. | 5.08 cm. | 66.5 | 33.5 | 69.2 | 300 |
| 6 | 150 | 3.1 (72% excess) | 1.1 | 25.4 cm. | 25.4 cm. | 9.0 | 91.0 | 77.8 | 2,000 |

(1) 20% and 37% aqueous HCl were used in runs 1 and 2-6, respectively.
(2) Measured from the top of the column reactor.
(3) Yield was calculated from the amount of HCl reacted to form $CH_3Cl$.

In accordance with at least some of the objects of the present invention, it has been shown that large quantities of alkyl halide, for example, methyl chloride, can be obtained as a by-product in the reaction of a dialkyldialkoxysilane and hydrogen chloride when the dialkyldialkoxysilane and hydrogen halide are introduced into a column containing hydrogen halide under reflux in such proportions that the amount of hydrogen halide introduced into the column is at a stoichiometric excess relative to the dialkyldialkoxysilane introduced into the column. The yield of cyclic organopolysiloxanes is substantially high without the use of a cracking step to obtain the cyclic organopolysiloxanes. Furthermore, in accordance with at least some of the objects of the present invention, it has been shown that the amount of alkyl halide product and the amount and type of organosiloxane product in the reaction of a dialkyldialkoxysilane and a hydrogen halide can be controlled by varying the temperature of the hydrogen halide undergoing reflux in the reactor column; varying the location of the respective hydrogen halide and dialkyldialkoxysilane feed points in the reactor column; and varying the stoichiometric excess of the hydrogen halide in the column relative to the amount of dialkyldialkoxysilane in the column.

While the invention has been described with respect to preferred embodiments, it will be apparent that certain modifications and changes can be made without departing from the spirit and scope of the invention and, therefore, it is intended that the foregoing disclosure be limited only by the claims appended hereto.

What is claimed is:

1. An improved process for making an alkyl halide and organosiloxanes from a dialkyldialkoxysilane and a hydrogen halide, comprising, simultaneously introducing the dialkyldialkoxysilane and hydrogen halide into a column containing hydrogen halide under reflux in such proportions that the amount of hydrogen halide introduced into the column is at a stoichiometric excess relative to the dialkyldialkoxysilane introduced into the column.

2. The process of claim 1 further comprising heating the column at a temperature sufficient to reflux the hydrogen halide introduced into the column and thereafter introducing the hydrogen halide into the column.

3. The process of claims 1 or 2 wherein the hydrogen halide in the column is heated at about 120° C. to about 175° C.

4. The process of claims 1 or 2 further comprising heating a reboiler containing hydrogen halide at a temperature sufficient to cause the hydrogen halide in the reboiler to reflux in the column and thereafter introducing the dialkyldialkoxysilane and hydrogen halide into the column.

5. The process of claim 4 wherein the hydrogen halide in the reboiler is heated at a tempeature of about 120° C. to about 175° C.

6. The process of claims 1, 2 or 4 wherein the dialkyldialkoxysilane is dimethyldimethoxysilane.

7. The process of claims 1, 2 or 4 wherein the hydrogen halide is anhydrous hydrogen chloride.

8. The process of claims 1, 2 or 4 wherein the hydrogen halide is aqueous hydrogen chloride.

9. The process of claim 1 wherein hydrogen halide is introduced into the column at a stoichiometric excess of about 15% to about 75% over the dialkyldialkoxysilane introduced into the column.

10. The process of claims 1, 2 or 4 wherein the dialkyldialkoxysilane is introduced into the column at a feed point located in the upper region of the column; the hydrogen halide is introduced into the column at a feed point located between the top of the column and the bottom of the column; and the hydrogen halide is maintained at reflux at a temperature of about 150° C. to about 175° C. whereby the yield of alkyl halide improves as the amount of hydrogen halide is increased from about a 15% to about a 60% stoichiometic excess over the amount of dialkyldialkoxysilane.

11. The process of claims 1, 2 or 4 wherein the dialkyldialkoxysilane and the hydrogen halide are introduced into the column at respective feed points located in the upper region of the column, and the hydrogen halide is maintained at reflux at a temperature of about 150° C. to about 175° C., whereby the yield of alkyl halide is about 99% when the hydrogen halide is fed into the column at a stoichiometric excess of about 50% over the dialkyldialkoxysilane.

12. The process of claims 1, 2 or 4 wherein the dialkyldialkoxysilane is introduced into the column at a feed point located in the upper region of the column; the hydrogen halide is introduced into the column at a feed point located in the lower region of the column; and the hydrogen halide is maintained at reflux at a temperature of about 150° C. to about 175° C., whereby the yield of cyclic organosiloxanes is greater than about 70% by weight of the organosiloxane composition when the hydrogen halide is fed into the column at a stoichiometric excess of about 15% to about 50% over the amount of dialkyldialkoxysilane fed into the column.

13. The process of claims 10, 11 or 12 wherein the dialkyldialkoxysilane is dimethyldimethoxysilane, and the hydrogen halide is hydrogen chloride.

14. A process for controlling the amount of alkyl halide product and the amount and type of organosiloxane product in the reaction of a dialkyldialkoxysilane and a hydrogen halide, comprising:
(a) providing hydrogen halide under reflux in a column having at least one dialkyldialkoxysilane feed point and at least one hydrogen halide feed point between the top of the column and the bottom of the column;
(b) varying the location of the respective hydrogen halide and dialkyldialkoxysilane feed points in the column;
(c) introducing hydrogen halide and dialkyldialkoxysilane into the column in such proportions that the amount of hydrogen halide introduced into the column is at a stoichiometric excess relative to the dialkyldialkoxysilane introduced into the column; and
(d) varying the stoichiometric excess of the hydrogen halide.

15. The process of claim 14 further comprising varying the temperature of the hydrogen halide under reflux in the column.

16. The process of claims 14 or 15 further comprising heating a reboiler containing hydrogen halide at a temperature sufficient to cause the hydrogen halide in the reboiler to reflux in the column and thereafter introducing the dialkyldialkoxysilane and hydrogen halide into the column.

17. The process of claims 14, 15 or 16 wherein the hydrogen halide is hydrogen chloride; the dialkyldialkoxysilane is dimethyldimethoxysilane; and the alkyl halide is methyl chloride.

18. The process of claims 14, 15, 16 or 17 wherein the hydrogen halide is aqueous hydrogen chloride.

19. The process of claim 15 wherein the temperature is about 120° C. to about 175° C.

20. The process of claim 15 wherein the temperature is about 150° C. to about 175° C.

21. The process of claims 14, 15, 16 or 17 wherein the hydrogen halide and dialkyldialkoxysilane are introduced into the column at respective feed points located in the upper region of the column, and the amount of hydrogen halide is introduced at from about a 15% to about a 60% stoichiometric excess over the amount of dialkdialkoxysilane, whereby the amount of alkyl halide product is increased, and the amount of organosiloxane products of the cyclic type is substantially greater than the linear type.

22. The process of claims 14, 15, 16 or 17 wherein the hydrogen halide and dialkyldialkoxysilane are introduced into the column at respective feed points in the column, one of which respective feed points is located in the upper region of the column and the other of which respective feed points is located in the lower region of the column, and the amount of hydrogen halide introduced into the column is from about a 15% to about a 60% stoichiometric excess over the amount of dialkyldialkoxysilane, whereby the amount of organosiloxane products of the cyclic type is substantially greater than the amount of the linear type.

23. The process of claims 14, 15, 16 or 17 wherein the hydrogen halide and dialkyldialkoxysilane are introduced into the column at respective feed points located in the lower region of the column, and the hydrogen halide is introduced in an amount at from about a 15% to about a 75% stoichiometric excess over the amount of dialkyldialkoxysilane, whereby the amount of organosiloxane products of the linear type is substantially greater than the amount of the cyclic type.

24. The process of claims 14, 15, 16 or 17 further comprising heating a reboiler containing hydrogen halide at a temperature sufficient to maintain the hydrogen halide in the reboiler at a temperature of about 120° C. to about 175° C.

25. A process for controlling the amount of methyl chloride product and the amount and type of cyclic and linear organosiloxane products in the reaction of a dimethyldimethoxysilane and hydrogen chloride, comprising:
   (a) providing hydrogen chloride under reflux in a column having at least one dimethyldimethoxysilane feed point between the top of the column and the bottom of the column and at least one hydrogen chloride feed point between the top of the column and the bottom of the column; and
   (b) introducing hydrogen chloride and dimethyldimethoxysilane into the column at respective feed points located in the upper region of the column, the amount of hydrogen chloride being introduced at from about a 15% to about a 60% stoichiometric excess over the amount of dimethyldimethoxysilane, whereby the amount of methyl chloride product is increased, and the amount of organosiloxane product of the cyclic type is substantially greater than the linear type; or introducing hydrogen chloride and dimethyldimethoxysilane into the column at respective feed points in the column, one of which respective feed points is located in the upper region of the column and the other of which respective feed points is located in the lower region of the column, the amount of hydrogen chloride being introduced at from about a 15% to about a 60% stoichiometric excess over the amount of dimethyldimethoxysilane, whereby the amount of organosiloxane product of the cyclic type is substantially greater than the amount of the linear type; or introducing hydrogen chloride and dimethyldimethoxysilane into the column at respective feed points located in the lower region of the column, the amount of hydrogen chloride being introduced at from about a 15% to about a 75% stoichiometric excess over the amount of dimethyldimethoxysilane, whereby the amount of organosiloxane product of the linear type is substantially greater than the amount of the cyclic type.

* * * * *